(12) United States Patent
Andersen et al.

(10) Patent No.: US 9,683,931 B2
(45) Date of Patent: Jun. 20, 2017

(54) APPARATUS FOR DETECTING A COMPONENT IN A SAMPLE

(71) Applicant: Radiometer Mediccal ApS, Brønshøj (DK)

(72) Inventors: Willy Lindegaard Andersen, Espergærde (DK); Heine Hansen, Ølstykke (DK); Oluf Dannevang, Glostrup (DK); Ole Munch Hansen, Brønshøj (DK)

(73) Assignee: Radiometer Medical ApS, Brønshøj (DK)

( * ) Notice: Subject to any disclaimer, the term of this patent is extended or adjusted under 35 U.S.C. 154(b) by 0 days.

(21) Appl. No.: 14/653,947

(22) PCT Filed: Dec. 17, 2013

(86) PCT No.: PCT/IB2013/061031
§ 371 (c)(1),
(2) Date: Jun. 19, 2015

(87) PCT Pub. No.: WO2014/097141
PCT Pub. Date: Jun. 26, 2014

(65) Prior Publication Data
US 2015/0316471 A1   Nov. 5, 2015

(30) Foreign Application Priority Data
Dec. 20, 2012 (DK) ................... 2012 00816

(51) Int. Cl.
*G01N 33/48* (2006.01)
*G01N 21/31* (2006.01)
(Continued)

(52) U.S. Cl.
CPC .......... *G01N 21/31* (2013.01); *G01N 21/274* (2013.01); *G01N 21/314* (2013.01); *G01N 33/49* (2013.01)

(58) Field of Classification Search
CPC ...... G01N 21/31; G01N 21/314; G01N 21/49; G01N 21/05; G01N 33/4925;
(Continued)

(56) References Cited

U.S. PATENT DOCUMENTS

| 4,805,623 A | 2/1989 | Jöbsis |
| 5,368,816 A * | 11/1994 | Detzer .................... F24F 3/16 422/172 |

(Continued)

FOREIGN PATENT DOCUMENTS

| AU | 2012 200 332 A1 | 2/2012 |
| JP | 04-001556 | 1/1992 |

(Continued)

OTHER PUBLICATIONS

International Search Report for International Application No. PCT/IB2013/061031, Apr. 24, 2014.
(Continued)

*Primary Examiner* — Michael P Stafira
(74) *Attorney, Agent, or Firm* — Finnegan, Henderson, Farabow, Garrett & Dunner, llp

(57) ABSTRACT

An apparatus for detecting a first component in a sample, the first component being responsive to at least radiation of a first wavelength, the sample comprising the first component and a second component responsive to at least radiation of a second wavelength.

32 Claims, 3 Drawing Sheets

(51) Int. Cl.
*G01N 33/49* (2006.01)
*G01N 21/27* (2006.01)

(58) Field of Classification Search
CPC ..... G01N 2021/0346; G01N 2021/036; G01N 2021/3148; G01N 21/359; G01N 15/1475; G01N 21/255; G01N 21/59; G01N 2015/1472
See application file for complete search history.

(56) References Cited

U.S. PATENT DOCUMENTS

| | | | | |
|---|---|---|---|---|
| 5,371,020 A | * | 12/1994 | Frischauf | G01N 21/0303 356/246 |
| 5,503,148 A | * | 4/1996 | Pologe | A61B 5/14551 128/925 |
| 5,836,883 A | * | 11/1998 | Tsuchiya | G01N 21/49 356/39 |
| 5,898,487 A | * | 4/1999 | Hage | G01N 21/532 356/39 |
| 6,084,661 A | * | 7/2000 | Mendelson | G01N 21/314 250/343 |
| 2005/0036147 A1 | | 2/2005 | Sterling et al. | |
| 2005/0094127 A1 | * | 5/2005 | O'mahony | A61B 5/14557 356/39 |
| 2006/0012774 A1 | * | 1/2006 | O'Mahony | A61M 1/1692 356/39 |

FOREIGN PATENT DOCUMENTS

| | | |
|---|---|---|
| JP | 04-332535 | 11/1992 |
| JP | 2001-516019 | 9/2001 |
| JP | 3500207 | 12/2003 |
| JP | 2006-523846 | 10/2006 |
| WO | WO 89/01758 | 3/1989 |
| WO | WO 99/00935 | 1/1999 |
| WO | WO 99/09395 | 2/1999 |
| WO | WO 2004/091387 | 10/2004 |
| WO | WO 2004/091387 A2 | 10/2004 |

OTHER PUBLICATIONS

Office Action of related Japanese Patent Application No. 2015-547260, dated May 6, 2016.
English language abstract for JP 04-001556, Jan. 7, 1992.
English language abstract for JP 04-332535, Nov. 19, 1992.

* cited by examiner

US 9,683,931 B2

APPARATUS FOR DETECTING A COMPONENT IN A SAMPLE

This application is a national stage filing under 35 U.S.C. §371 of International Application No. PCT/IB2013/061031, filed on Dec. 17, 2013, which claims priority to PA201200816, filed on Dec. 20, 2012. The contents of these applications are each incorporated herein by reference.

TECHNICAL FIELD

Disclosed herein are embodiments of an apparatus for detecting a component in a sample and, in particular, embodiments of such an apparatus for detecting a component in sample by measuring absorbance of radiation by the sample.

BACKGROUND

Photometric methods for detecting components in a sample, such as a sample of blood, by exposing the sample to radiation and by measuring the absorbance of the radiation by the sample are well known.

For example, such methods are widely used within the field of diagnostic analysis to determine concentrations of body constituents based on optical measurements. The Lambert-Beer's law applies to optical measurements where the transmission of radiation from a radiation source through a sample is determined by a detector, i.e. the absorbance is proportional to the concentration of absorbing species in the sample as well as to the sample thickness, i.e. the path length of the radiation path through the sample. The proportionality factor is referred to as the extinction coefficient.

Application of the Lambert-Beer's law to determine constituents of unknown concentration thus requires knowledge of the path length (along or in combination with the extinction coefficient).

In a measuring apparatus the path length is often defined by the dimensions of a sample chamber. When such chambers have a long lifetime and may be used for a large number of measurements, the dimensions may be determined, e.g. during a calibration process using a sample having a constituent of a known concentration. The same applies to sample chambers that may be manufactured with a high degree of precision. However, when the sample chambers have a shorter life time or when their dimensions are not stable over time or vary from chamber to chamber, frequent calibrations are required, thus resulting in a decreased efficiency of the measuring system. Nevertheless, it may be desirable to use sample chambers having a shorter lifetime, single-use sample chambers, or sample chambers being manufactured with larger tolerances, as these may be considerably less expensive to manufacture.

U.S. Pat. No. 6,442,411 discloses a method of in vivo analysis of blood constituents like hemoglobin and glucose. This prior art method uses the water content in blood samples as an internal reference for the purpose of determining the optical path length by means of a differential determination of water during the systolic and diastolic portions of the arterial pulsation. According to U.S. Pat. No. 6,442,411, the variability of the water concentration in blood is 1.8% around the average level. Whereas such level of precision may suffice in some applications, it would generally be desirable to further increase the precision of the measurements of concentrations of constituents of a sample. For example, for many in vitro analysis purposes, a higher precision is often desired.

SUMMARY

According to one aspect, disclosed herein are embodiments of an apparatus for detecting a first component in a sample, the first component being responsive to at least radiation of a first wavelength, the sample comprising the first component and a second component responsive to at least radiation of a second wavelength. Embodiments of the apparatus comprise:

at least one radiation source configured to direct radiation towards the sample;

at least one radiation detector configured to detect radiation of at least the first and the second wavelength, said detected radiation having propagated along a radiation path through at least a portion of the sample; and a processing unit operable to receive at least one detector signal from the at least one radiation detector indicative of the detected radiation.

Embodiments of the processing unit are further configured to determine an estimated path length of the radiation path at least from a determined absorbance by the sample of radiation at the second wavelength;

determine an estimated concentration of the first component at least from a determined absorbance by the sample of radiation at the first wavelength and from the estimated path length;

determine a corrected concentration of the first component at least from the estimated concentration and from a correction term indicative of a corrected path length corrected for a presence of the first component using the estimated concentration.

The concentration of the first component is computed based on an absorbance measurement at a first wavelength to which the first component is responsive and based on an estimated path length that is determined from an absorbance measurement at a second wavelength to which a second component of the sample is responsive. The estimated path length is corrected for the presence of the first component in the sample. Consequently, a more accurate determination of the radiation path length is achieved which, in turn, results in a more accurate determination of the concentration of the first component.

In particular, in the context of measuring constituents of blood samples, the present inventors have found that, although the water concentration of blood samples displays a rather low variability, typically in the range of a few percent, a determination of the radiation path length based thereon is insufficient in many applications and, in particular, for purposes of accurate in vitro analysis of blood constituents. In this context the present inventors have found that the water concentration in blood is biased by the presence of certain blood components, in particular of hemoglobin constituents of the blood.

Accordingly, with the present invention a correction of the calculated results based on an improved determination of the radiation path length is provided. This allows for a determination of the length of the radiation path of a measuring chamber of a measuring device to be made with an improved precision, i.e. by taking into account the bias originating from certain blood constituents. While some embodiments of the apparatus may explicitly determine the corrected path lengths, it will be understood that such explicit calculation may not be necessary, e.g. in embodiments where only the determination of the concentration of the first component is desired. In many situations it may thus suffice to apply a correction term to the initially estimated concentration where the correction term compensates for the inaccuracy of the initially estimated path length. For example the correction term may be a correction factor to be multiplied with the initially estimated concentration so as to obtain the corrected concentration. The correction term may be determined from a function that models the impact of the concentration of the first component on the absorbance at the second wavelength. The correction term may be calculated as a function of the estimated concentration of the first component and from one or more predetermined model parameters. The model parameters may be predetermined during a calibration process. The model parameters may be determined for one apparatus and used in a plurality of other apparatus.

Thus, with embodiments of the apparatus and methods described herein, a blood sample may be investigated in that the absorbance by a blood component of radiation of a certain first wavelength is determined along with the absorbance by the water content of the sample of radiation of a certain second wavelength. Generally, absorbance may be defined as the negative logarithm, e.g. $\log_{10}$, of a ratio of an output intensity of radiation and the corresponding input intensity of radiation.

Based on the measured absorbance at the second wavelength, embodiments of the apparatus and methods described herein determine an initial estimate of the length of the radiation path. Thus, the apparatus determines, from the absorbance by water of radiation of the second wavelength, an estimated length of the radiation path.

Subsequently, based on the estimated path length of the radiation path, an estimated concentration of a first component of the sample is determined from its absorbance of radiation of the first wavelength. The present inventors have found that relating these estimated values allows for a determination of the length of the radiation path and, thus, a determination of the concentration of the first component with significantly improved precision.

Some embodiments of the apparatus may be for in vivo measurements while other embodiments of the apparatus may be for in vitro measurements. In some embodiments, in particular those for in vitro measurements, the apparatus comprises a sample chamber for accommodating the sample, the sample chamber defining the radiation path. For example, the sample chamber may be a sample vessel such as a tube, a cuvette or the like. At least a part of the walls defining the sample chamber are made of a transparent material so as to allow the radiation to enter and exit the sample chamber.

In some embodiments, the apparatus comprises an actuator operable to change the path length of the radiation path between at least a first and a second path length; and wherein the processing unit is operable to determine a concentration of the first component from a difference of absorbance measurements at the first wavelength measured with the path length set to the first path length and the second path length, respectively. Consequently, the measurements may be corrected for absorbance and other artifacts that do not depend on the radiation path length through the sample, e.g. absorbance of walls defining the sample chamber.

It will be appreciated that the choice of the first and second wavelengths may depend on the components to detect in the sample, as different sample constituents are responsive to different wavelengths. In particular, the first wavelength will generally be different from the second wavelength. In some embodiments, the first wavelength is selected such that the second component is not responsive to the first wavelength; in particular, any absorption peaks in the absorbance spectrum of the second component are displaced from the first wavelength. Similarly, the second wavelength may be selected such that the first component is not responsive to the second wavelength. In some embodiments, e.g. in the context of detecting hemoglobin constituents in blood samples, the first wavelength lies between 100 nm and 1400 nm, such as in the visible range between 390 nm and 750 nm, such as between 450 nm and 700 nm. In some embodiments, the second wavelength lies in the infrared range between 750 nm and 1 mm, such as between 1400 nm and 1 mm, such as between 4100 nm and 4400 nm. For example, when the second component is water the first wavelength may be selected below 1400 nm where water has no significant absorption while the second wavelength may be selected above 1400 nm where water absorbs radiation. It will further be appreciated that the concentrations of the first and/or second components may be determined based on absorbance measurements at multiple wavelengths. Moreover, it will be appreciated that measurement at a wavelength may comprise measurement within a wavelength interval, e.g. an interval around a center wavelength. The width of the interval may e.g. depend on a wavelength selectivity of the detector or detectors used for detecting radiation that has passed through the sample.

In some embodiments, the processing unit is further operable to determine a concentration of a third component of the sample, the third component being responsive to at least radiation of a third wavelength, from the absorbance of the sample at the third wavelength, from the estimated path length, and from a correction term indicative of a corrected path length corrected for a presence of the first component using the estimated concentration of the first component. Hence, embodiments of the apparatus disclosed herein may be used to determine concentrations of multiple components based on the corrected path length that has been corrected for the presence of the first component. In the context of hemoglobin measurements of blood samples, examples of such further components may include hemoglobin derivatives, bilirubin, and/or the like.

Alternatively, when the second component is water or another solvent, and when the concentration of a third component is to be measured relative to the water/solvent rather than relative to the entire sample, a correction of the estimated path length may not be necessary, and the concentration of the third component may advantageously be computed based on the estimated, uncorrected path length. For example, in the case of blood samples, measurement of the $CO_2$ concentration in the blood water phase may be desirable. When the estimation of the path length is based on the absorbance of water, a correction of this path length, e.g. for the presence of hemoglobin, may not be necessary for the purpose of determining the $CO_2$ determination.

It will further be appreciated that the method may be applied to perform correction of the radiation path length due to the presence of multiple components, e.g. a first and a third component. In such an embodiment, the method may comprise estimating respective concentrations of the first and third component based on respective absorbance measurements and based on the estimated path length, and determining a correction term as a function of the estimated concentrations of the first and third components and on one or more model parameters.

The at least one radiation source may comprise a single radiation source emitting radiation at both the first and second wavelength. Alternatively, the at least one radiation source comprises a first radiation source configured to produce at least radiation at the first wavelength, and a second radiation source configured to produce at least radiation at the second wavelength. It will be appreciated that the radiation source or radiation sources may include further components e.g. filters, interferometers, a device for controlling an operational parameter of the light source and/or the like. The apparatus may further comprise one or more elements for redirecting radiation of the first or second wavelength so as to cause the radiation of the first and second wavelength to propagate through the sample along radiation paths having the same path length, e.g. along a common radiation path. In an embodiment comprising separate light sources, the apparatus may comprise a beam combiner configured to direct radiation from the first radiation source and radiation from the second radiation source along a common radiation path through the sample. Examples of suitable radiation sources may depend on the desired wavelength range and may include, a lamp for producing visible light, UV light, infrared light, a laser, a light emitting diode, a gas lamp, e.g. a xenon lamp, etc.

Similarly, the at least one radiation detector may comprise a single detector responsive to radiation of the first and second wavelengths. Alternatively, the apparatus may comprise a first radiation detector configured to detect at least radiation at the first wavelength, and a second radiation detector configured to detect at least radiation at the second wavelength. To this end some embodiments of the apparatus comprise a beam splitter configured to direct a first part of the radiation from the sample to the first radiation detector and a second part of the radiation from the sample to the second detector. Examples of suitable radiation detectors may depend on the desired wavelength range and may include a photosensitive detector, a spectrometer, etc.

In some embodiments, the radiation sources and radiation detectors may be arranged on opposite sides of the sample. Alternatively, one or more of the detectors may be located on the same side of the sample as the corresponding radiation source. For example, the radiation may be directed through the sample and redirected by a suitable optical element, e.g. a mirror or grating, towards the detector, thus passing through the sample again. In such an embodiment, the radiation path length is the length of the total radiation path back and forth through the sample.

Disclosed herein are different aspects including the apparatus described above and in the following, corresponding methods, devices, and/or product means, each yielding one or more of the benefits and advantages described in connection with the first mentioned aspect, and each having one or more embodiments corresponding to the embodiments described in connection with the first mentioned aspect and/or disclosed in the appended claims.

According to one aspect, disclosed herein is a method for determining a concentration of a first component in a sample, the first component being responsive to at least radiation of a first wavelength, the sample comprising the first component and a second component responsive to at least radiation of a second wavelength, the method comprising:

receiving a measured first absorbance of the sample at at least the first wavelength and a measured second absorbance of the sample at at least the second wavelength;

determining, at least from the second absorbance, an estimated path length of a radiation path along which the radiation has propagated through the sample;

determining an estimated concentration of the first component at least from the first absorbance and from the estimated path length;

determining a corrected concentration of the first component at least from the estimated concentration and from a correction term indicative of a corrected path length corrected for a presence of the first component using the estimated concentration.

According to another aspect, disclosed herein is a method for determining a path length of a radiation path along which radiation has propagated through a sample, the sample comprising a first component responsive to radiation at at least a first wavelength, and a second component responsive to radiation at at least a second wavelength, the method comprising:

receiving a measured first absorbance of the sample at at least the first wavelength, and a measured second absorbance of the sample at at least the second wavelength;

determining, at least from the second absorbance, an estimated path length of a radiation path along which the radiation has propagated through the sample;

determining an estimated concentration of the first component at least from the first absorbance and from the estimated path length;

correcting the estimated path length for a presence of the first component using the estimated concentration of the first component.

Consequently, the corrected path length may subsequently be used in the calculation of the concentrations of multiple other sample components based on respective absorbance measurements.

The features of embodiments of the methods described herein may be implemented in software and carried out on a signal or data processing system or other data and/or signal processing device, such as a processing unit of an apparatus for determining a component of a sample, caused by the execution of computer-executable instructions. The instructions may be program code means loaded in a memory, such as a Random Access Memory (RAM), from a storage medium or from another computer via a computer network. Alternatively, the described features may be implemented by hardwired circuitry instead of software or in combination with software.

The processing unit may be any circuitry or device configured to perform data processing, e.g. a suitably programmed microprocessor, a CPU of a computer, of an apparatus for determining a component of a sample, or of another processing device, a dedicated hardware circuit, etc., or a combination of the above. The processing unit may comprise or be communicatively coupled to a memory or other suitable storage medium having computer program code stored thereon adapted to cause, when executed by the processing unit, the processing unit to perform the steps of embodiments of the method described herein.

Accordingly, according to one aspect, disclosed herein are embodiments of a signal or data processing apparatus configured to perform the steps of an embodiment of the method described herein. The signal or data processing system may be a suitably programmed data processing system, e.g. a suitably programmed computer, or a suitably programmed or otherwise configured apparatus for processing output signals from radiation detectors.

In some embodiments, the signal or data processing apparatus comprises at least one radiation source configured to direct radiation towards a sample; at least one radiation detector configured to detect radiation of at least the first and the second wavelength, said detected radiation having propagated along a radiation path through at least a portion of the sample. For example, the apparatus may be a photometric analyzer for blood samples or other samples, e.g. for use in clinical diagnostics.

According to yet another aspect, disclosed herein are embodiments of a computer program comprising program code configured to cause a signal or data processing system to perform the steps of the method disclosed herein, when the program code is executed by the data processing system. The computer program may be embodied as a computer readable medium having stored thereon a computer program. Examples of a computer readable medium include a magnetic storage medium, a solid state storage medium, an optical storage medium or a storage medium employing any other suitable data storage technology. In particular, examples of storage media include a hard disk, a CD Rom or other optical disk, an EPROM, EEPROM, memory stick, smart card, etc.

In some embodiments, the method comprises determining the correction term from an absorption model for determining the second absorbance as being related to the path length by a suppression term, wherein the suppression term changes with changing concentration of the first component. In particular, the absorption model may be a linear model and the method may comprise determining the correction term from an absorption model for determining the second absorbance as being proportional to the path length and related to the path length by a factor of proportionality, wherein the factor of proportionality decreases, between a maximum factor and a minimum factor, with increasing concentration of the first component. In some embodiments, the correction term may be a correction factor and determining the corrected concentration of the first component may comprise multiplying the estimated concentration of the first component with the correction factor. In some embodiments, the correction term, e.g. the correction factor, may be a function of the estimated concentration of the first component and one or more predetermined model parameters. The predetermined model parameters may be determined from a number of calibration measurements, e.g. of samples with varying concentrations of the first component, where the concentrations of the first component are known, e.g. from suitable reference measurements. The correction factor may be represented as a polynomial function of the estimated concentration of first component. It has been found that representing the correction factor as a linear function of the estimated concentration of first component results in an accurate determination of the concentration of the first component.

Embodiments of the methods and apparatus may be applied to determine concentrations of a number of components in a number of types of samples, such as body fluids, liquids, etc. In some embodiments, the method and apparatus disclosed herein are applied to measurements with the field of clinical diagnostics, e.g. an apparatus for analyzing blood or other samples. In some embodiments, the first component is an analyte and the second component is a solvent such as water. In some embodiments, the first component is hemoglobin, bilirubin, and a derivative of hemoglobin. It will further be appreciated that some embodiments of the method disclosed herein may perform corrections of the path length for more than one component, e.g. for both hemoglobin and albumin in blood samples.

BRIEF DESCRIPTION OF THE DRAWINGS

The above and/or additional objects, features and advantages of embodiments of the methods, systems and devices disclosed herein, will be further elucidated by the following illustrative and non-limiting detailed description of embodiments of the methods, systems and devices disclosed herein, with reference to the appended drawings, wherein.

DETAILED DESCRIPTION

In the following description, reference is made to the accompanying figures, which show by way of illustration how embodiments of the methods, systems and devices disclosed herein may be practiced.

Figure 1:
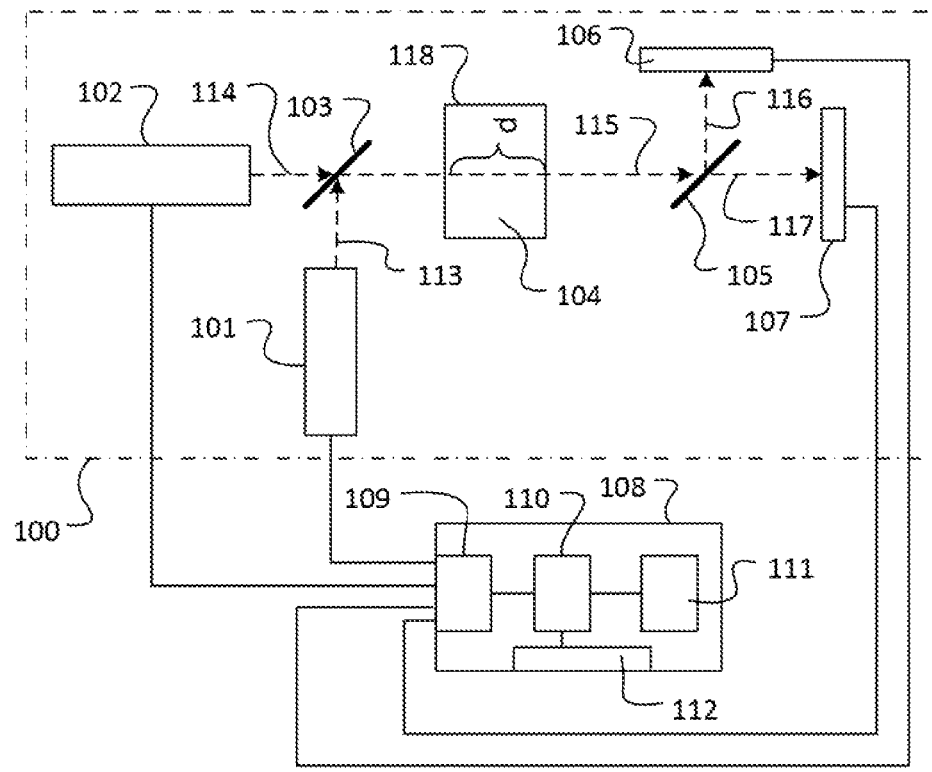
FIG. 1 schematically illustrates an embodiment of an apparatus for determining a component in a sample.

FIG. 1 schematically illustrates an embodiment of an apparatus for determining a component in a sample. The apparatus comprises a measurement module 100 and signal processing module 108. These functional modules may be located in the same enclosure so as to form an integrated apparatus or they may otherwise be structurally integrated with each other. Alternatively, they may be implemented as separate entities that may be communicatively connected with each other. The measurement module 100 performs absorbance measurements of a sample 104 and forwards the measurement results to the signal processing module 108 which performs signal analysis and computes at least a concentration of a first component of the sample.

The measurement unit comprises a first radiation source 101 and a second radiation source 102 adapted to output radiation of at least a first and a second wavelength, respectively. The radiation 113 from radiation source 101 and the radiation 114 from radiation source 102 are combined by a beam combiner 103 and directed through the sample 104 to be analyzed. To this end, the sample 104 is accommodated in a sample chamber 118 and located in the path of the combined radiation 113 and 114. The radiation thus propagates through the sample 104 along a radiation path having a path length d. The sample 104 absorbs a portion of the incoming radiation while another portion 115 exits the sample. The radiation 115 from the sample is split into two parts 116 and 117, respectively, by a beam splitter 105. Part beam 116 is directed onto a first radiation detector 106, while part beam 117 is directed onto a second radiation detector 107. The detector signals from detectors 106 and 107 are fed to the signal processing module 108.

The signal processing module 108 comprises interface circuitry 109, e.g. a data acquisition board or other suitable circuitry, for receiving detector signals from radiation detectors 106 and 107. The signal processing module may further be operable as a control unit. To this end, the signal processing module 108 may further be connected, via the interface circuitry 109, to the radiation sources 101 and 102 and, optionally, to other controllable elements of the measuring module 100, e.g. to tunable filters, and/or the like. The signal processing module 108 further comprises a processing unit 110, e.g. a CPU, coupled to the interface circuitry 109 and suitably programmed or otherwise configured to compute the concentration of a desired component of the sample. To this end, the processing unit is operable to perform the steps of an embodiment of the method described herein, e.g. the embodiment described with reference to FIG. 4. The signal processing module 108 further comprises a memory 111 or other storage medium for storing model parameters and/or program code or use by the processing unit 110. The processing unit 108 further comprises an output interface 112, e.g. a display or data communication interface unit, for outputting the calculated concentration. The memory 111 and the output interface 112 are each communicatively coupled to the processing unit 110.

It will be appreciated that, in alternative embodiments, the functions performed by the measurement module 100 and the signal processing module 108, respectively, may be distributed in a different manner. For example, the measurement module may perform some of the signal processing and forward processed data to the signal processing unit.

The radiation sources 101 and 102 may comprise suitable filters or may otherwise be configured to output radiation of substantially the first and second wavelengths, respectively, e.g. radiation of a narrow frequency band around the first and second wavelengths, respectively. Alternatively, one or each of the radiation sources may emit radiation over a broader wavelength range so as to allow the recording of a spectrum of intensities as a function of wavelength.

In yet alternative embodiments, the apparatus may include a single radiation source and/or a single radiation detector where the radiation source or the single radiation detector is adapted to emit/detect radiation both at the first and second wavelengths.

In the context of determining hemoglobin in blood samples, the first radiation source 101 may be adapted to output visible light. In particular, the first wavelength may be at a suitable absorbance peak associated with hemoglobin in the visible part of the spectrum e.g. at 576.5 nm or an isobestic wavelength. The second radiation source may emit light in the infrared part of the electromagnetic spectrum and, in particular, a part of the spectrum where water absorbs radiation. For example, the second wavelength may be in the range between 4100 nm and 4400 nm e.g. at 4308 nm.

The radiation detectors 106 and 107 may detect the intensity of the radiation 116 and 117, respectively, where the detector 106 is sensitive to at least radiation at the first wavelength and the detector 107 is sensitive to at least radiation at the second wavelength. The apparatus is also configured to measure reference intensities $I_0$, e.g. by performing a measurement without the sample 104 being located in the radiation path, so as to compute an absorbance from a corresponding measured intensity with the sample positioned in the beam path and from a corresponding reference intensity. In an embodiment where the absorbance is measured at different path lengths and a difference of absorbance values is calculated, an explicit measurement of $I_0$ is not required.

Figure 2:
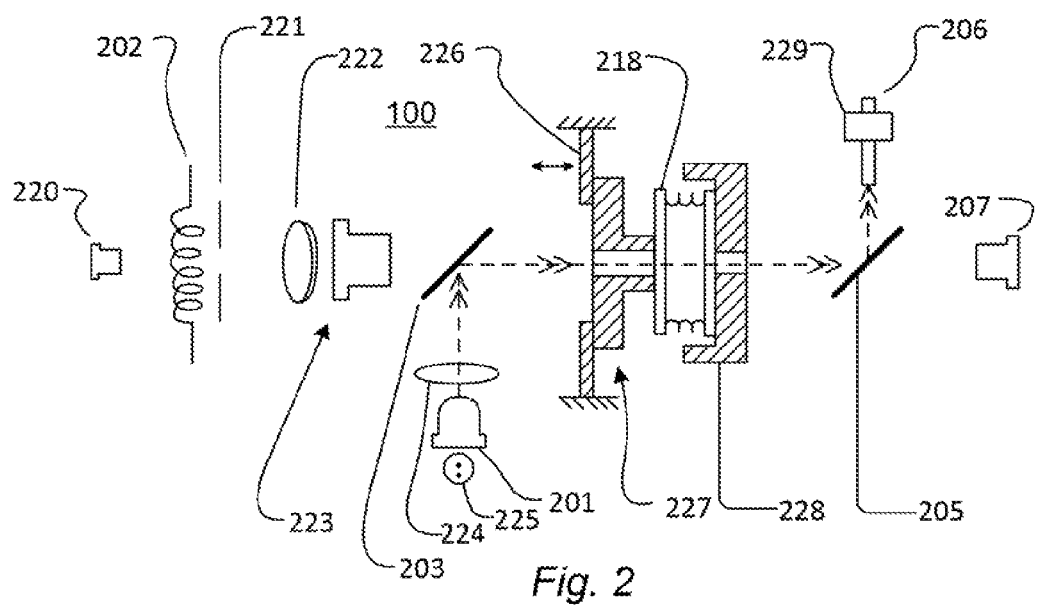
FIG. 2 schematically illustrates an embodiment of a measurement module of an apparatus for determining a component in a sample.

With reference to FIG. 2, an embodiment of a measurement module 100 will now be described. In particular, FIG. 2 illustrates an embodiment of a measurement module 100 for detecting constituents such as hemoglobin in a sample of blood. The measurement module 100 of FIG. 2 is similar to the measurement module of FIG. 1 and it comprises first and second radiation sources 201 and 202, a beam combiner 203, a sample chamber 218, a beam splitter 205, and radiation detectors 206 and 207, all as described in connection with FIG. 1.

The radiation source 201 is a light emitting diode (LED) emitting light in the visible range, e.g. white light. The light from radiation source 201 is directed via a lens 224 onto the beam combiner 203 and through the sample chamber 218 such that the light from the radiation sources 201 and 202 propagates through the sample chamber along a common radiation path. After passing through the sample chamber 218 the combined radiation is split up by beam splitter 205 into a first partial beam that is directed, via an optical fiber 229 onto the first radiation detector 206, in this example a spectrometer configured to detect the intensity of the incoming light at multiple wavelengths, and into a second part beam directed onto the second radiation detector 207, in this example a lead selenide detector for detecting IR radiation. The measurement module further comprises a xenon lamp 225 that is used for calibrating the wavelength of the spectrometer 206.

The radiation source 202 is an infrared source whose output is directed through an aperture 221, and a lens 222 to an interferometer 223, e.g. a Fabry-Perot interferometer. The interferometer 223 may be controlled by a control unit to generate infrared light of varying wavelength thus allowing recording of a scan over a range of the infrared spectrum. The output from the interferometer 223 is directed via the beam combiner 203 through the sample chamber 218. In alternative embodiments, the interferometer may be omitted. For example, the detector 207 may be a combined interferometer and detector. In yet an alternative embodiment, the interferometer 207 may be replaced by an optical band pass filter. In particular, this may be sufficient when the measurement module is not to be used for detection of components responsive to infrared radiation, but where the measurement in the infrared part of the spectrum is merely used for the purpose of determining the radiation path length.

The measurement module further comprises a reference diode 220 allowing measurement and setting of the temperature of the IR source 202. An example of suitable radiation sources, optical elements and detectors for measuring absorbance of blood in the infrared range are also disclosed in U.S. Pat. No. 5,371,020 which is hereby incorporated herein in its entirety by reference.

In the example of FIG. 2, the sample chamber is accommodated in a sample holder comprising a hemolyzer 227, a tilt bed 228, and a path length modulator 226. The sample chamber is sandwiched between the hemolyzer 227 and the tilt bed 228 in the direction along the optical axis. The hemolyzer 227 and the tilt bed 228 each have an aperture so as to allow radiation to path through the sample. The path length modulator 226 is arranged to actuate the hemolyzer 227 towards the tilt bed 228 thereby causing the sample chamber 218 to be compressed, thus resulting in a reduced path length of the radiation through the sample chamber 218. When the path length modulator 226 does not actuate the hemolyzer 227, the sample chamber 218 reverts to its previous shape and size. Consequently, the apparatus is configured to measure absorbance at two or more different radiation path lengths, e.g. as described in U.S. Pat. No. 5,371,020.

Generally, the sample chamber 218 may be compressible along the direction of the radiation path, and the actuator may be configured to impart a force on a side wall of the sample chamber 218 while an opposite side wall rests against a support member, e.g. tilt bed 228. The actuator may thus cause the side walls to be pushed towards each other, thus changing the path length of the radiation path. For example, the actuator may be a piezoelectric element.

The hemolyzer 227 may comprise a piezoelectric actuator, acting on a displaceable member or directly on the sample chamber 218. The piezoelectric actuator may be configurable to cause mechanical vibrations, e.g. at frequencies in the ultrasound range, along the optical axis which are transmitted on the sample chamber, e.g. as described in U.S. Pat. No. 3,972,614. The vibrations cause the red blood cells in the blood sample to rupture, thereby preventing undesired scattering of the radiation.

Figure 3:
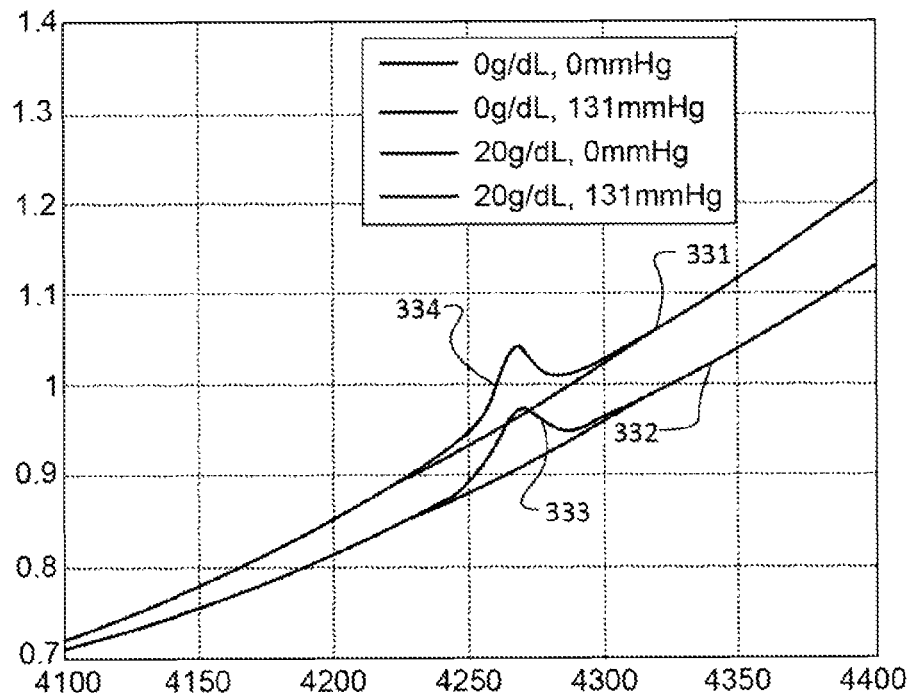
FIG. 3 illustrates the effect of the presence of hemoglobin in a blood sample on the measured absorbance at wavelengths to which water is responsive.

FIG. 3 illustrates the effect of the presence of hemoglobin in a blood sample on the measured absorbance at wavelengths to which water is responsive. In particular, FIG. 3 shows absorbance spectra 331 and 332 of blood samples comprising 0 g/dL and 20 g/dL hemoglobin, respectively. As can be clearly seen from FIG. 3, the presence of hemoglobin reduces the measured absorbance. FIG. 3 further shows absorbance spectra for the corresponding samples but with 131 mmHg $CO_2$ in the water. $CO_2$-related absorbance peaks 333 and 334 can clearly been seen.

Figure 4:
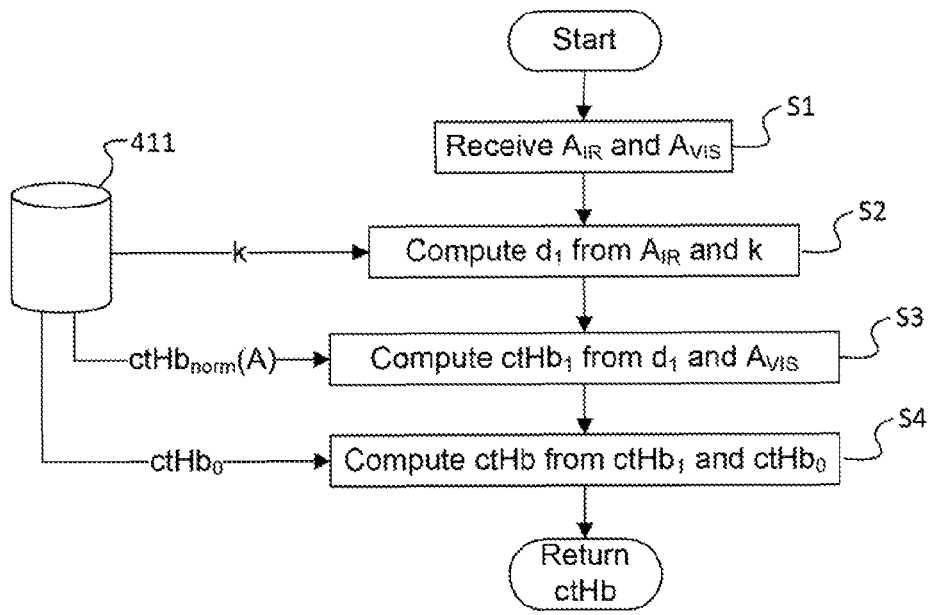
FIG. 4 shows a flow diagram of an embodiment of a method for determining a component in a sample.

FIG. 4 shows a flow diagram of an embodiment of a method for determining a component in a sample. In particular the process of FIG. 4 determines the concentration of hemoglobin in a blood sample. The process may be performed by the processing unit 110 of FIG. 1 in response to received detector signals from the measurement module 100 of FIG. 1 or FIG. 2.

In initial step S1, the process receives an absorbance measurement $A_{VIS}$ of a sample of blood at a first wavelength to which hemoglobin is responsive, e.g. at 576.5 nm. The process further receives an absorbance measurement $A_{IR}$ of the blood sample measured at a suitable second wavelength in the IR range of the spectrum, e.g. at 4308 nm, and with the same radiation path length as the measurement of $A_{VIS}$.

In step S2 the process estimates an estimated path length $d_1$ of the radiation path, e.g. based on the relation $$d_1 = k \cdot A_{IR}, \quad (1)$$

where k is a constant that may be determined during an initial calibration, e.g. by measuring absorbance of a sample fluid, e.g. water, at a known radiation path length or by performing multiple measurements at different known radiation path lengths and by performing a linear regression analysis. The constant k may be stored in a memory 411 accessible to the processing unit performing the method, e.g. memory 111 of FIG. 1.

In step S3, the process computes an estimated hemoglobin concentration $ctHb_1$ from the measured absorbance $A_{VIS}$ and from the estimated path length $d_1$. To this end, the processing unit may have stored a function for computing a normalized concentration $ctHb_{norm}$ from the measured absorbance $A_{VIS}$ and for a given reference/normalized path length $d_0$. This function may use Beer's law and a predetermined extinction factor $\epsilon$, which again may be determined from calibration measurements, e.g. according to $$ctHb_{norm}(A) = A / (\epsilon \cdot d_0) = \text{const.} \cdot A$$

The function $ctHb_{norm}(A)$ for calculating $ctHb_{norm}$ from a measured absorbance may be stored in a memory 411 accessible to the processing unit, e.g. memory 111 of FIG. 1.

The estimated concentration $ctHb_1$ for the estimated path length $d_1$ may thus be calculated as $$ctHb_1 = ctHb_{norm}(A_{VIS}) \cdot d_0 / d_1. \quad (2)$$

In step S4, the process computes a corrected hemoglobin concentration ctHb from the estimated concentration $ctHB_1$ and from a correction factor that corrects for the error in the estimation of the estimated path length $d_1$ caused by the presence of hemoglobin in the sample. This error is caused by the effect of hemoglobin on the measured absorbance in the IR region as was illustrated in FIG. 3.

The correction factor may be determined from a suitable parameterized model of the effect of the hemoglobin on the infrared absorbance $A_{IR}$.

In one embodiment, the model may take the effect of hemoglobin on the absorbance AIR into account by a linear correction term:

$$A_{IR} = (d/k) \cdot (1 - ctHb/ctHb_0). \quad (3)$$

Here, d is the true path length, k is the above-mentioned constant, ctHb is the true hemoglobin concentration, and $ctHb_0$ is a model parameter indicating a maximum hemoglobin concentration where the sample would not cause water-related IR absorption at all.

The absorption model of eqn. (3) thus determines the absorbance $A_{IR}$ as being related to the path length d by a suppression term $(1 - ctHb/ctHb_0)/k$, wherein the suppression term depends on the hemoglobin concentration ctHb. In particular, the absorbance $A_{IR}$ is modeled to be proportional to the path length d with the above suppression term as the factor of proportionality, i.e. the factor of proportionality decreases, between a maximum factor $1/k$ and a minimum factor 0, with increasing hemoglobin concentration.

The model parameter $ctHb_0$ may be determined from absorbance measurements at different known hemoglobin concentrations, e.g. by performing a regression based on measured absorbance values and from hemoglobin concentrations determined by a suitable reference measurement technique, such as the HiCN reference method as described in "Reference methods for the quantitative determination of hemoglobin in blood samples"; NCCLS (CLSI) Publication H15-A3. Villenova, Pa.: NCCLS, 2000. The thus determined model parameter $ctHb_0$ may be stored in memory 411 accessible to the processing unit, e.g. memory 111 of FIG. 1.

Noting that the true hemoglobin concentration ctHb is related to the true path length d by $ctHb = ctHb_{norm} \cdot d_0 / d$, it follows from eqns. (1)-(3) that $$ctHb = ctHb_1 / (1 + ctHb_1 / ctHb_0). \quad (4)$$

Hence, equation (4) allows calculating the true concentration ctHb from the estimated concentration $ctHb_1$ obtained in step S3 and from the model parameter $ctHb_0$ of the absorbance model of eqn. (3).

Using eqn. (4) and the predetermined model parameter $ctHb_0$, in step S4 the process thus calculates a corrected hemoglobin concentration ctHb.

Optionally, the process may compute the corrected path length explicitly:

$$d = d_1 (ctHb_0 + ctHb_1) / ctHb_0.$$

It will be appreciated that the above process may be performed in a different fashion and the predetermined parameters used in the computation may be represented in different ways.

For example, equation (4) may be approximated by a polynomial expression:

$$ctHb = ctHb_1(a_1 + a_2 ctHb_1) + O((ctHb_1/ctHb_0)^3), \quad (5)$$

where coefficients $a_1$ and $a_2$ have been introduced, and where $O((ctHb_1/ctHb_0)^3)$ designates a residual term of order 3. Hence, instead of determining the parameter $ctHb_0$ during an initial calibration procedure, the process may be based on two model parameters $a_1$ and $a_2$, that may be determined based on a quadratic regression against hemoglobin concentrations determined by a suitable reference method. An example of such a calibration process will be described below. Consequently, in an alternative embodiment of the process of FIG. 4, step S4 uses equation (5) instead of equation (4) and predetermined coefficients $a_1$ and $a_2$ that have been determined during an initial calibration process and stored in memory 411 accessible to the processing unit.

In yet an alternative embodiment, the measurements may be made using the apparatus of FIG. 2 where the path length is modulated by modulator 226 and where differences of absorbance values are measured with the radiation path length set to different values, and where the calculations are based on the difference in absorbance and the corresponding difference in path lengths, e.g. as described in U.S. Pat. No. 5,371,020.

In particular, in some embodiments, the processing unit is operable to determine an estimated path length difference between the first and second path lengths at least from respective absorbance measurements at the second wavelength;

determine the estimated concentration of the first component at least from a difference of absorbance measurements at the first wavelength measured with the path length set to the first path length and the second path length, respectively, and from the estimated path length difference;

determine a corrected concentration of the first component at least from the estimated concentration and from a correction term indicative of a corrected path length difference between the first and second path lengths corrected for a presence of the first component using the estimated concentration.

Hence, both the initial estimation of the path length and the concentration, and the correction may be based on the difference in path length, thus providing a particularly accurate determination of the concentration of the first component.

It will further be appreciated that corrected concentrations of hemoglobin derivatives, bilirubin and or other constituents may be computed in a similar fashion, i.e. from an initial estimated concentration, estimated based on an estimated path length and an absorbance measurement at a suitable wavelength, and subsequently corrected for the presence of hemoglobin as described above.

Moreover, it will be appreciated that the $A_{IR}$ measurements at wavelengths at the $CO_2$ peak shown in FIG. 3 may be used to obtain both an estimated path length $d_1$ and a measurement of the $CO_2$ concentration. A method for determining the $CO_2$ concentration has been described in U.S. Pat. No. 5,371,020. For example, in one embodiment, absorbance measurements at 4228 nm, 4268 nm and 4308 nm may be used for a determination of both the $CO_2$ concentration and for a determination of $d_1$.

EXAMPLE

Figure 5:
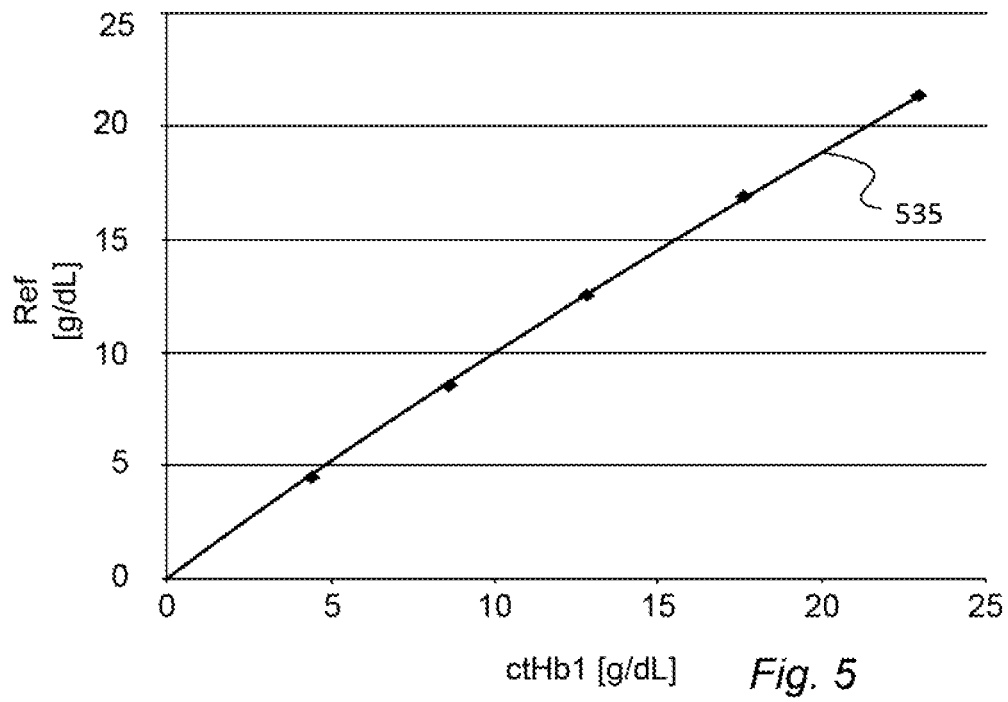
FIG. 5 illustrates the determination of parameters of a correction factor.

With reference to FIG. 5, an example of the determination of the model parameters $a_1$ and $a_2$ will now be described.

The absorbance $A_{IR}$ of a sample of water with a known path length of $d_0=0.1$ mm and at a wavelength of 4308 nm was measured to be $A_{IR}=1.0385$ using a Perkin Elmer FT2000 IR-spectrometer. Consequently, the constant k was determined as $k=0.1$ mm$/1.0385=96.29$ μm @$\lambda=4308$ nm.

The normalized hemoglobin concentration $ctHb_{norm}$ was determined from measured absorbance values of samples in a cavity having a known path length of $d_0=0.1$ mm, and at a wavelength of 576.5 nm using Lambert-Beer's law: $A=\epsilon*ctHb_{norm}*d_0$, where $\epsilon$ is the extinction factor of hemoglobin. Using $\epsilon=15.425*(mM*cm)$, M=mol/L, O2Hb, $\lambda=576.5$ nm from Zijlstra extinction data (see W G Zijlstra et al.: "Absorption spectra of Human Fetal and Adult Oxyhemoglobin, De-oxyhemoglobin, Carboxyhemoglobin, and Methemoglobin", Clin. Chem. 37/9, 1633-1638, 1991), the concentration is $ctHb_{norm}$ [g/dL]=A*10.57 g/dL, (as 1 g/dL=0.62058 mM).

For a given IR absorbance $A_{IR}$ the estimated hemoglobin concentration as a function of measured absorbance $A_{VIS}$ may be written as $ctHb_1=ctHb_{norm}*d_0/d_1=A_{VIS}*10.57*100/(A_{IR}*96.29)=A_n*10.98$ g/dL where a normalized absorbance $A_n=A_{VIS}/A_{IR}$ has been introduced.

For different samples having a number of different hemoglobin concentrations, the absorbance values $A_{IR}$ and $A_{VIS}$ have been measured by an apparatus as described in connection with FIG. 2, except that the apparatus used in this example did not include a hemolyzer and that the modulator was driven by a stepper motor via a threaded shaft; instead of the hemolyzer, the blood samples were chemically hemolyzed prior to the measurements using 3-[(3-cholamidopropyl)dimethylammonio]-2-hydroxy-1-propanesulfonate (CHAPSO). For the same samples, the hemoglobin concentrations have been measured using a reference method; these reference concentrations are referred to as $ctHb_{ref}$.

Based on these measurement points the coefficients of eqn. (5) have been determined by a regression of ctHb calculated from eqn. (5) against the reference values $ctHb_{ref}$.

FIG. 5 and table 1 show the result of the regression, resulting in coefficients $a_1=1.041139$, $a_2=-0.004911$. In FIG. 5, the dots represent the data points for $ctHb_1$ against ctHbref, while the curve 435 shows the regression curve $ctHb=ctHb_1 (a_1+a_2 ctHb_1)$.

TABLE 1

Regression with hemoglobin correction of path length (concentrations in g/dL); corresponding to a correlation $R^2 = 0.999982$.

| ctHb_Ref | An | ctHb1 | ctHb | Diff |
|---|---|---|---|---|
| 0.02 | 0.000 | 0.00 | 0.00 | −0.02 |
| 4.45 | 0.396 | 4.35 | 4.44 | −0.02 |
| 8.51 | 0.779 | 8.55 | 8.54 | 0.04 |
| 12.53 | 1.168 | 12.82 | 12.54 | 0.02 |
| 16.87 | 1.605 | 17.62 | 16.82 | −0.05 |
| 21.33 | 2.095 | 23.01 | 21.35 | 0.02 |
| | | | Mean | 0.00 |
| | | | Stdev | 0.03 |

The thus determined parameters correspond to a value of $ctHb_0=-1/(a_2/a_1)=212$ g/dL.

Figure 6:
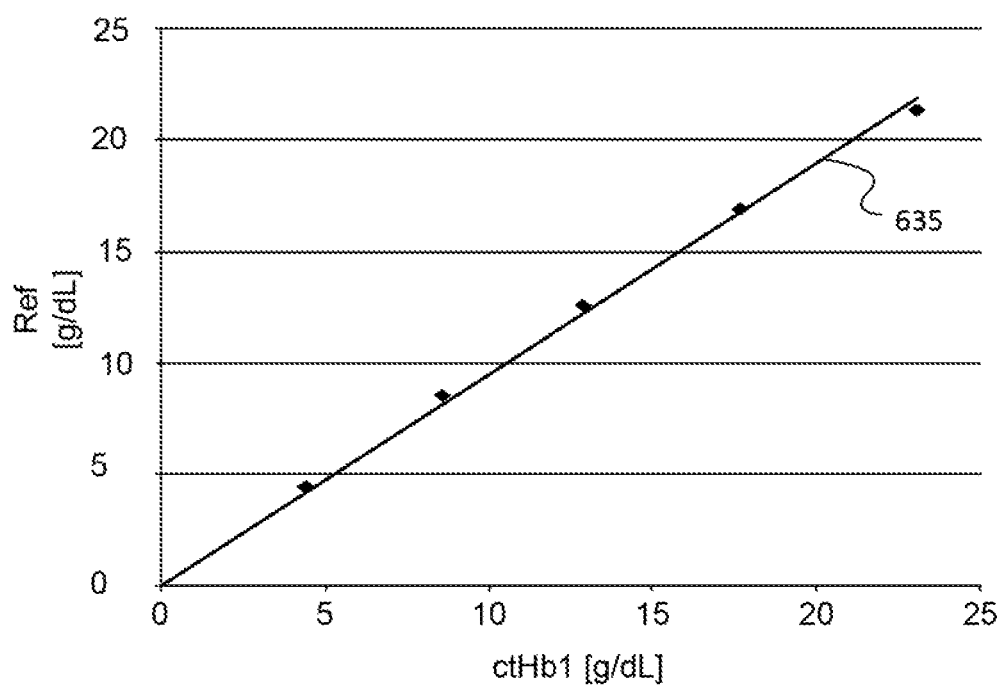
FIG. 6 illustrates a comparative example of a calibration without correction for hemoglobin content.

If the correction term $a_2*ctHb1$ in eqn. (5) is omitted (corresponding to omitting the correction term dependent on ctHb0 in eqn. (4)), a considerably lower correlation between the calculated values ctHb and reference values $ctHb_{ref}$ is obtained, as illustrated by FIG. 6 and table 2 below. This corresponds to a linear regression $ctHb=a_1*ctHb_1$ (curve 635 in FIG. 6)

TABLE 2

Regression result without hemoglobin correction of path length (concentrations in g/dL), corresponding to a correlation $R^2 = 0.997875$.

| ctHb_Ref | An | ctHb1 | ctHb | Diff |
|---|---|---|---|---|
| 0.02 | 0.000 | 0.00 | 0.00 | −0.02 |
| 4.45 | 0.396 | 4.35 | 4.13 | −0.32 |
| 8.51 | 0.779 | 8.55 | 8.12 | −0.39 |
| 12.53 | 1.168 | 12.82 | 12.18 | −0.35 |
| 16.87 | 1.605 | 17.62 | 16.73 | −0.15 |
| 21.33 | 2.095 | 23.01 | 21.84 | 0.51 |
| | | | Mean | −0.12 |
| | | | Stdev | 0.34 |

Thus, a comparison of the results of tables 1 and 2 illustrates that the correction described herein results in an improved determination of the hemoglobin concentration ctHb.

Although some embodiments have been described and shown in detail, the aspects disclosed herein are not restricted to them, but may also be embodied in other ways within the scope of the subject matter defined in the following claims. In particular, it is to be understood that other embodiments may be utilized and structural and functional modifications may be made. In particular, embodiments of the aspects disclosed herein have mainly been described with reference to the determination of hemoglobin in blood samples. It will be understood, however, that embodiments of the methods, devices and products described herein may also be applied to the determination of other constituents of blood samples, of samples of other types of body fluids and/or of other types of samples both in diagnostic applications and other analytical applications, e.g. within environmental or food analysis.

In device claims enumerating several means, several of these means can be embodied by one and the same item of hardware. The mere fact that certain measures are recited in mutually different dependent claims or described in different embodiments does not indicate that a combination of these measures cannot be used to advantage.

It should be emphasized that the term "comprises/comprising" when used in this specification is taken to specify the presence of stated features, integers, steps or components but does not preclude the presence or addition of one or more other features, integers, steps, components or groups thereof.

The invention claimed is:

1. An apparatus for detecting a component in a sample comprising, a first component being responsive to at least radiation of a first wavelength, the sample comprising the first component and a second component responsive to at least radiation of a second wavelength, the apparatus comprising:
   at least a first radiation source configured to produce at least radiation at the first wavelength, and a second radiation source configured to produce at least radiation at the second wavelength, and a beam combiner configured to direct radiation from the first radiation source and radiation from the second radiation source along a common radiation path through the sample;
   at least one radiation detector configured to detect radiation of at least the first and the second wavelength, said detected radiation having propagated along a radiation path through at least a portion of the sample; and
   a processing unit operable to receive at least one detector signal from the at least one radiation detector indicative of the detected radiation, and to
      determine an estimated path length of the radiation path at least from a determined absorbance by the sample of radiation at the second wavelength;
      determine an estimated concentration of the first component at least from a determined absorbance by the sample of radiation at the first wavelength and from the estimated path length;
   determine a corrected concentration of the first component at least from the estimated concentration and from a correction term indicative of a corrected path length corrected for a presence of the first component using the estimated concentration.

2. The apparatus according to claim 1 further comprising a sample chamber for accommodating the sample, the sample chamber defining the radiation path.

3. The apparatus according to claim 2, comprising an actuator operable to change the path length of the radiation path between at least a first and a second path length; and wherein the processing unit is operable to determine a concentration of the first component from a difference of absorbance measurements at the first wavelength measured with the path length set to the first path length and absorbance measurements at the first wavelength measured with the path length set to the second path length.

4. The apparatus according to claim 3, wherein the processing unit is operable to
   determine an estimated path length difference between the first and second path lengths at least from respective absorbance measurements at the second wavelength;
   determine the estimated concentration of the first component at least from a difference of absorbance measurements at the first wavelength measured with the path length set to the first path length and absorbance measurements at the first wavelength measured with the path length set to the second path length, and from the estimated path length difference;
   determine a corrected concentration of the first component at least from the estimated concentration and from a correction term indicative of a corrected path length difference between the first and second path lengths corrected for a presence of the first component using the estimated concentration.

5. The apparatus according to claim 1, wherein the processing unit is further operable to determine a concentration of a third component of the sample, the third component being responsive to at least radiation of the third wavelength, at least from the absorbance of the sample at the third wavelength, from the estimated path length, and from a correction term indicative of a corrected path length corrected for a presence of the first component using the estimated concentration of the first component.

6. The apparatus according to claim 1, wherein the processing unit is further operable to determine a concentration of a third component of the sample, the third component being responsive to at least radiation of a third wavelength, at least from the absorbance of the sample at the third wavelength and from the estimated path length.

7. The apparatus according to claim 1 wherein the at least one radiation detector comprises a first radiation detector configured to detect at least radiation at the first wavelength, and a second radiation detector configured to detect at least radiation at the second wavelength.

8. The apparatus according to claim 7, comprising a beam splitter configured to direct a first part of the radiation from the sample to the first radiation detector and a second part of the radiation from the sample to the second detector.

9. A method for determining a concentration of a component in a sample comprising, a first component being responsive to at least radiation of a first wavelength, the sample comprising the first component and a second component responsive to at least radiation of a second wavelength, the method comprising:
   combining the radiation of the first wavelength and the second wavelength using a beam combiner and then directing the combined radiation through the sample;
   receiving a measured first absorbance of the sample at at least the first wavelength and a measured second absorbance of the sample at at least the second wavelength;

determining, at least from the second absorbance, an estimated path length of a radiation path along which the radiation has propagated through the sample;

determining an estimated concentration of the first component at least from the first absorbance and from the estimated path length;

determining a corrected concentration of the first component at least from the estimated concentration and from a correction term indicative of a corrected path length corrected for a presence of the first component using the estimated concentration.

10. The method according to claim 9, comprising determining the correction term from an absorption model for determining the second absorbance as being related to the path length by a suppression term, wherein the suppression term changes with changing concentration of the first component.

11. The method according to claim 10, comprising determining the correction term from an absorption model for determining the second absorbance as being proportional to the path length and related to the path length by a factor of proportionality, wherein the factor of proportionality decreases, between a maximum factor and a minimum factor, with increasing concentration of the first component.

12. The method according to claim 9, further comprising determining a concentration of a third component of the sample, the third component being responsive to at least radiation of a third wavelength, at least from the absorbance of the sample at the third wavelength, from the estimated path length, and from a correction term indicative of a corrected path length corrected for a presence of the first component using the estimated concentration of the first component.

13. The method according to claim 9, further comprising determining a concentration of a third component of the sample; the third component being responsive to at least radiation of a third wavelength, at least from the absorbance of the sample at the third wavelength and from the estimated path length.

14. A method for determining a path length of a radiation path along which radiation has propagated through a sample comprising:

(a) the sample comprising a first component responsive to radiation at at least a first wavelength, and a second component responsive to radiation at at least a second wavelength, the method comprising:

(b) receiving a measured first absorbance of the sample at at least the first wavelength, and a measured second absorbance of the sample at at least the second wavelength;

(c) determining, at least from the second absorbance, an estimated path length of a radiation path along which the radiation has propagated through the sample;

(d) determining an estimated concentration of the first component at least from the first absorbance and from the estimated path length; and (e) correcting the estimated path length for a presence of the first component using the estimated concentration of the first component; and (g) applying the result from step (e) to correct concentration of the first component during clinical diagnostics.

15. The method according to claim 14, wherein the estimated path length is corrected by a correction term determined from an absorption model for determining the second absorbance as being related to the path length by a model parameter, wherein the model parameter changes with changing concentration of the first component.

16. The method according to claim 15, wherein the correction term is determined from an absorption model for determining the second absorbance as being proportional to the path length where the factor of proportionality decreases, between a maximum factor and a minimum factor, with increasing concentration of the first component.

17. The method according to claim 14, wherein the first component is an analyte and the second component is a solvent.

18. The method according to claim 7, wherein the solvent is water.

19. The method according to claim 17, wherein the analyte is chosen from total hemoglobin, bilirubin, and a derivative of hemoglobin.

20. The method according to claim 14, wherein determining the estimated path length comprises determining the estimated path length from the first absorbance and a predetermined proportionality factor.

21. A signal or data processing apparatus configured to perform the steps of the method of claim 14.

22. The signal or data processing apparatus according to claim 21, further comprising at least one radiation source configured to direct radiation towards a sample; at least one radiation detector configured to detect radiation of at least the first and the second wavelength, said detected radiation having propagated along a radiation path through at least a portion of the sample.

23. A computer program comprising program code configured to cause a data processing system to perform the steps of the method of claim 14, when the program code is executed by the data processing system.

24. A computer readable medium having stored thereon a computer program according to claim 23.

25. The method according to claim 9, wherein the first component is an analyte and the second component is a solvent.

26. The method according to claim 25, wherein the solvent is water.

27. The method according to claim 25, wherein the analyte is chosen from total hemoglobin, bilirubin, and a derivative of hemoglobin.

28. The method according to claim 9, wherein determining the estimated path length comprises determining the estimated path length from the first absorbance and a predetermined proportionality factor.

29. A signal or data processing apparatus configured to perform the steps of the method of claim 9.

30. The signal or data processing apparatus according to claim 29, further comprising at least one radiation source configured to direct radiation towards a sample; at least one radiation detector configured to detect radiation of at least the first and the second wavelength, said detected radiation having propagated along a radiation path through at least a portion of the sample.

31. A computer program comprising program code configured to cause a data processing system to perform the steps of the method of claim 9, when the program code is executed by the data processing system.

32. A computer readable medium having stored thereon a computer program according to claim 31.

* * * * *